United States Patent
Notestein et al.

(10) Patent No.: US 9,024,076 B2
(45) Date of Patent: May 5, 2015

(54) ALKANE OXIDATION

(75) Inventors: Justin M. Notestein, Evanston, IL (US); Nicholas J. Schoenfeldt, Chicago, IL (US); Andrew W. Korinda, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/353,453

(22) PCT Filed: Jul. 18, 2012

(86) PCT No.: PCT/US2012/047121
§ 371 (c)(1),
(2), (4) Date: Apr. 22, 2014

(87) PCT Pub. No.: WO2013/062645
PCT Pub. Date: May 2, 2013

(65) Prior Publication Data
US 2014/0296578 A1 Oct. 2, 2014

Related U.S. Application Data

(60) Provisional application No. 61/550,595, filed on Oct. 24, 2011.

(51) Int. Cl.
| | |
|---|---|
| *C07C 45/30* | (2006.01) |
| *C07C 29/48* | (2006.01) |
| *B01J 31/22* | (2006.01) |
| *B01J 31/16* | (2006.01) |
| *B01J 31/18* | (2006.01) |
| *C07C 407/00* | (2006.01) |
| *C07C 45/28* | (2006.01) |

(52) U.S. Cl.
CPC .......... *B01J 31/2217* (2013.01); *B01J 31/1616* (2013.01); *B01J 31/1633* (2013.01); *B01J 31/182* (2013.01); *B01J 31/2239* (2013.01); *B01J 2231/70* (2013.01); *B01J 2531/0208* (2013.01); *B01J 2531/0211* (2013.01); *B01J 2531/0219* (2013.01); *B01J 2531/0258* (2013.01); *B01J 2531/72* (2013.01); *C07C 407/00* (2013.01); *C07C 2101/14* (2013.01); *C07C 29/48* (2013.01); *C07C 45/28* (2013.01); *C07C 45/30* (2013.01)

(58) Field of Classification Search
CPC ........... C07C 45/28; C07C 29/48; B01J 31/00
USPC .......................... 568/490, 911; 502/155, 167
See application file for complete search history.

(56) References Cited

U.S. PATENT DOCUMENTS

| | | | |
|---|---|---|---|
| 5,516,738 A | 5/1996 | Jureller et al. | |
| 7,049,388 B2 | 5/2006 | Boriack et al. | |
| 2003/0054949 A1 | 3/2003 | Chang et al. | |
| 2005/0065378 A1 | 3/2005 | Bosch et al. | |

FOREIGN PATENT DOCUMENTS

EP    0970951    1/2000

OTHER PUBLICATIONS

International Search Report and Written Opinion for related PCT Application PCT/US2012/047121, mailed Nov. 14, 2012 (11 pgs).
Nicholas J. Schoenfeldt, et al.: "A heterogeneous, selective oxidation catalyst based on Mn triazacyclononane grafted under reaction conditions", Chemical Communications, vol. 46, No. 10, Jan. 1, 2010 (4 pgs).
Georgiy B. Shul'Pin, et al.: Oxidations by the system 'hydrogen peroxide-[Mn2L203] [PF6]2 (L=1,4,7-trimethyl-1,4,7-triazacyconane) -carboxylic acid. Part 10: Co-catalytic effect of different carboxylic acids in cyclohexanol, and acetone TETRAHEDRON, vol. 64, No. 9, (10 pgs), 2008.
Mac Leod T C O, et al.: "Mild oxidation of alkanes and toluene by tert-butylhydroperoxide catalyzed by an homogeneous and immobilized Mn (salen) complex", Applied Catalysis A: General, Elsevier Science, Amsterdam, NL, vol. 372, No. 2, Jan. 15, 2010 (8 pgs).
Nicholas J. Schoenfeldt, et al.: "Solid Cocatalysts for Activating Manganese Triazacyclononane Oxidation Catalysts", ACS Catalysis, col. 1, No. 12, Oct. 20, 2011 (12 pgs).
Georgiy Shul'Pin: "Hydrocarbon Oxygenations with Peroxides Catalyzed by Metal Compounds", Mini-Reviews in Organic Chemistry, 2009, 6, 95-104 (10 pgs).
Kevin F. Sibbons, et al. "The application of manganese complexes of ligands derived from 1,4,7-triazacyclononane in oxidative catalysis" Dalton Trans. 2006, 645-661 (17 pgs).
Galina V. Nizova, et al.: "Hydrocarbon Oxidations with Hydrogen Peroxide Catalyzed by a Soluble Polymer-Bound Manganese(IV)Complex with 1,4,7-Triazacyclononane" Adv. Synth, Catal. 2002, 344, 899-905 (7 pgs).
Ronald Hage, et al.: "Bleach and oxidation catalysis by manganese-1,4,7-triazacylononane complexes and hydrogen peroxide" Journal of Molecular Catalysis A: Chemical 251 (2006) 150-158 (9 pgs).
Georgiy B. Shul'pin, et al.: "Oxidations by the system "hydrogen peroxide—manganese(IV) complex—carboxylic acid". Part 3. Oxygenation of ethane, higher alkanes, alcohols, olefins and sulfides" Journal of Molecular Catalysis A: Chemical 170 (2001) 17-34 (18 pgs).

(Continued)

*Primary Examiner* — Sikarl Witherspoon
(74) *Attorney, Agent, or Firm* — Brooks, Cameron & Huebsch, PLLC

(57) ABSTRACT

Embodiments include an alkane oxidation catalyst having a support modified with a carboxylate group. The carboxylate group is functionalized with a manganese complex selected from the group consisting of $[(C_6H_{12}N_3R_3)Mn(OCH_3)_3]Z$, $[(C_6H_{12}N_3R_3)Mn_2O_3]Z_2$, $[(C_6H_{15}N_3)Mn_4O_6]Z_4$. Each R is independently an alkyl group having 1 to 3 carbons, and each Z is independently $PF_6^-$, $ClO_4^-$, or $Br^-$.

10 Claims, No Drawings

(56) References Cited

OTHER PUBLICATIONS

Johannes W. de Boer, et al.: "The role of salicylic acid, L-ascorbic acid and oxalic acid in promoting the oxidation of alkenes with H2O2 catalysed by [MnIV2(O)3(tmtacn)2]2+†" Dalton Trans., 2008, 6283-6295 (13 pgs).

Josef J. Dannacher "Catalutic bleach: Most valuable applications for smart oxidation chemistry" Journal of Molecular Catalysis A: Chemical 251 (2006) 159-176 (18 pgs).

John R. Lindsay Smith, et al.: "Manganese 1,4,7-trimethyl-1,4,7-triazacyclonane complexes: Versatile catalysts for the oxidation of organic compounds with hydrogen peroxide" Journal of Molecular Catalysis A: Chemical 251 (2006) 114-122 (9 pgs).

Dirk E. De Vos, et al.: "Epoxidation of Terminal or Electron-deficient Olefins with H2O2, catalysed by Mntrimethyltriazacyclonane Complexes in the Presence of an Oxalate Buffer" Tetrahedron Letters 39 (1998) 3221-3224 (4 pgs).

Georgiy B. Shul'pin, et al.: "Oxidations by the system "hydrogen peroxide—[Mn2L2O3][PF6]2 (L = 1,4,7-trimethyl-1,4,7-triazacyclononane)—oxalic acid". Part 6. Oxidation of methane and other alkanes and olefins in water" Journal of Organometallic Chemistry 690 (2005) 4498-4504 (7 pgs).

Hamdullah Kilic, et al.: "Effect of Additives on Chemoselectivity and Diastereoselectivity in the Catalytic Epoxidation of Chiral Allylic Alcohols with Hydrogen Peroxide and Binuclear Manganese Complexes" J. Org. Chem., 2009. 74, 1335-1140 (6 pgs).

Quee-Smith, et al.: "Synthesis, Structure, and Characterization of a Novel Manganese(IV) Monomer, [MnIV(Me3TACN)(OMe)3](PF6) (MeTACN) N, N¢, N¢¢-Trimethyl-1,4,7-triazacyclononane), and its Activity toward Olefin Oxidation with Hydrogen Peroxide" Inorg. Chem. 1996, 35, 6461-6465.

Y. V. Subba Rao, et al.: "Practical heterogenisation of an active manganese triazacyclonane epoxidation catalyst via surface glycidylation" Jan. 1, 2007.

Schoenfeldt, et al.:"Manganese Triazacyclononane Oxidation Catalysts Grafted under Reaction Conditions on Solid Cocatalytic Supports" IJ. Am. Chem. Soc. 2011, 133, 18684-18695.

Georgiy B. Shul'pin: "Metal-catalyzed hydrocarbon oxygenations in solutions: the dramatic role of additives: a review" Journal of Molecular Catalysis A: Chemical 189 (2002) 39-66.

Georgiy B. Shurpin, et al.:"Oxidations by the "hydrogen peroxide—manganese(IV) complex—carboxylic acid " system. Part 4.y Efficient acid-base switching between catalase and oxygenase activities of a dinuclear manganese(IV) complex in the reaction with H2O2 and an alkane" New J. Chem., 2002, 26, 1238-1245.

Karl Wieghardt: "The Active Sites in Manganese-Containing Metalloproteins and Inorganic Model Complexes" Angew. Chem. Inr. Ed. Engl. 28 (1989) 1153-1172.

Karl Wieghardt, et al.: "Synthesis of a Tetranuclear Manganese(IV) Cluster with Adamantane Skeleton: f(C6H,5N3) 4Mn406j4+"Angew. Chem. Int. Ed. Engl. 22 (1983) No. 4.

Camile B. Woitiskia, et al.:"Oxidations by the system "hydrogen peroxide—dinuclear manganese(IV) complex—carboxylic acid" Part 5. Epoxidation of olefins including natural terpenes"Journal of Molecular Catalysis A: Chemical 222 (2004) 103-119.

Stephen J. Lippard: "Progress in Inorganic Chemistry" Department of Chemistry, Massachusetts Institute of Technology, vol. 35, pp. 1-8 , Sep. 2009.

Georgec Hristou:"Manganese Carboxylate Chemistry and Its Biological Relevance" Acc. Chem. Res. 1989, 22, 328-335.

Johannes W. de Boer, et al.: "Mechanism of Cis-Dihydroxylation and Epoxidation of Alkenes by Highly H2O2 Efficient Dinuclear Manganese Catalysts" Inorganic Chemistry, vol. 46, No. 16, 2007.

Jean H. Koek, et al.:"Improved syntheses, structures, spectral and electrochemical properties of [ Mn1"2(p-O) (p-02CMe)2L2] + and [ Mn1v2(p-O)3L2] + complexes. Two homologous series derived from eight N-substituted 1,4,7-triazacyclononanes J. Chem. SOC.D, alton Trans., 1996, pp. 353-362.

Lisa J. Lobree, et al.:"Investigations of the State of Fe in H—ZSM-5" Journal of Catalysis 186, 242-253 (1999).

Bjorn Moden, et al.:"Structural and Functional Characterization of Redox Mn and Co Sites in AlPO Materials and Their Role in Alkane Oxidation Catalysis" J. Phys. Chem. B 2004, 108, 5552-5563.

Natalia Morlanés, et al.:"Grafted Ta—calixarenes: Tunable, selective catalysts for direct olefin epoxidation with aqueous hydrogen peroxide" Journal of Catalysis 275 (2010) 191-201.

Justin M. Notestein, et al.:"Grafted Metallocalixarenes as Single-Site Surface Organometallic Catalysts" J. Am. Chem. Soc. 9 vol. 126, No. 50, 2004.

Dario Prieto-Centurion, et al.:"Surface speciation and alkane oxidation with highly dispersed Fe(III) sites on silica" Journal of Catalysis 279 (2011) 103-110.

Benoit Pugin, et al.:"Immobilized Complexes for Enantioselective Catalysis: When Will They Be Used in Industry?" Top Catal (2010) 53:953-962.

Lawrence Que Jr., et al.:"Biologically inspired oxidation catalysis" NATURE|vol. 455|Sep. 18, 2008.

ALKANE OXIDATION

This application is a National Stage Application under 35 U.S.C. §371 of International Application Number PCT/US2012/047121, filed Jul. 18, 2012 and published as WO 2013/062645 on May 2, 2013, which claims the benefit to U.S. Provisional Application 61/550,595, filed Oct. 24, 2011, the entire contents of which are incorporated herein by reference in its entirety.

This disclosure relates to an alkane oxidation catalyst and methods of forming an alkane oxidation product.

Alkane oxidation products are used in the production of plastics, fuels, nylons, pesticides, textiles, disinfectants, reagents, detergents, solvents, and others. Examples of alkane oxidation products include, but are not limited to, alcohols, aldehydes, ketones, and peroxides.

This disclosure provides an alkane oxidation catalyst including a support modified with a carboxylate group, where the carboxylate group is functionalized with a manganese complex.

The support may be a carbon support or an oxide support. Examples of the carbon support include, but are not limited to, activated carbon, which intrinsically contains a carboxylate group.

Examples of the oxide support include, but are not limited to, silicon dioxide ($SiO_2$), aluminum oxide ($Al_2O_3$), titanium silicon dioxide (Ti—$SiO_2$), aluminum silicate ($Al_2O_3$—$SiO_2$), titanium dioxide ($TiO_2$), and cerium dioxide ($CeO_2$).

The oxide support may be modified with the carboxylate group by depositing a silane group as an ester via heating the oxide support in refluxing pyridine to provide an ester-modified oxide support. The ester-modified oxide support may then be converted to carboxylic acid (CA) by heating the oxide support in refluxing aqueous solutions of mineral acid (e.g., hydrochloric acid (HCl)) to provide the support modified with the carboxylate group. Silane groups include, but are not limited to, 2-(carboxymethoxy)-ethyltrimethoxysilane and ethyl 4-(triethoxysilyl)benzoate. Materials synthesized in this way are identified as oxide support "—C" to denote surface carboxylates synthesized from 2-(carbomethoxy)ethyltrimethoxysilane (e.g., the support modified with the carboxylate group may be represented as $SiO_2$—C) and identified as oxide support "—B" to denote surface carboxylates synthesized from ethyl 4-(triethoxysilyl)benzoate (e.g., the support modified with the carboxylate group may be represented as $SiO_2$—B). Remaining hydroxyl (OH) groups can be capped with a variety of silanes, such as propyltriethoxysilane (propyl), n-octyltrimethoxysilane (octyl), mixtures of perfluorododecyl-1H,1H,2H,2H-triethoxysilane/perfluorotetradecyl-1H,1H,2H,2H-triethoxysilane (perfluro), or hexamethyldisilazane/trimethylchlorosilane(trimethyl) (e.g., the support modified with the carboxylate group may be represented as $SiO_2$—C-propyl, $SiO_2$—C-octyl, $SiO_2$—C-perfluoro, or $SiO_2$—C-trimethyl).

Alternatively, the oxide support may be modified with the carboxylate group by depositing ditopic molecules, including, but not limited to, terephthalic acid (TA) and 3,4-dihydroxyhydrocinnamic acid (DHHCA), which coordinate with oxide supports and provide a carboxylate functionalization with the manganese complex.

A density of the carboxylate groups on the support may be in a range of from 0.01 to 1 carboxylate groups per square nanometer (groups/$nm^2$) of oxide support "—C" or oxide support "—B" and in a range of from 1 to 6 groups/$nm^2$ for oxide supports modified by depositing ditopic molecules. This can be measured by absorption spectroscopy, thermogravimetric analysis, and/or nuclear magnetic resonance spectroscopy.

Examples of the manganese complex include, but are not limited to, [($C_6H_{12}N_3R_3$)Mn($OCH_3$)$_3$]Z, a monomeric manganese complex, [($C_6H_{12}N_3R_3$)$Mn_2O_3$]$Z_2$, a dimeric manganese complex, and [($C_6H_{15}N_3$)$Mn_4O_6$]$Z_4$, a tetrameric manganese complex. Each R is independently an alkyl group having 1 to 3 carbons. Examples of the alkyl groups include, but are not limited to, a methyl group, an ethyl group, and a propyl group. Each Z is independently hexafluorophosphate ($PF_6^-$), perchlorate ($ClO_4^-$), or bromine ($Br^-$). The carboxylate group can be functionalized with the manganese complex by bonding a manganese atom of the manganese complex to an oxygen atom of the carboxylate group. The manganese complex and the carboxylate groups on a surface of the support have a molar ratio in a range of from 1.0:0.3 to 1:20 manganese complex groups to carboxylate groups.

The alkane oxidation catalyst can be formed by combining the support modified with the carboxylate group that is functionalized with the manganese complex at a temperature in a range of from −10 degrees Celsius (° C.) to 50° C. in the presence of hydrogen peroxide. The alkane oxidation catalyst can be formed in the presence of a solvent. Examples of the solvent include, but are not limited to, acetonitrile, water, methanol, acetic acid, and acetone. The support is employed in a range of from 1 to 20 milligrams per milliliter of solvent (mg/mL). The manganese complex is employed in a range of from 0.1 to 1.0 milimole per liter of solvent (mM). Hydrogen peroxide is employed in a range of initial concentrations of from 0.1 to 0.5 moles per liter of solvent (M).

This disclosure provides a method for oxidizing an alkane. The method includes oxidizing the alkane by contacting the alkane with the alkane oxidation catalyst in the presence of hydrogen peroxide to provide an alkane oxidation product. Examples of the alkane oxidation product include, but are not limited to alcohols, ketones, aldehydes, and alkylhydroperoxides. The hydrogen peroxide and the alkane have a molar ratio in a range of from 3:1 to 1:20 where the hydrogen peroxide includes the initial hydrogen peroxide and/or subsequent hydrogen peroxide. The method can include employing a solvent. Examples of the solvent are discussed herein. The method conditions include oxidizing the alkane at a temperature in a range of from −10° C. to 50° C.

The method includes contacting a support modified with a carboxylate group with a manganese complex and hydrogen peroxide to functionalize the carboxylate group with the manganese complex to form an alkane oxidation catalyst. The alkane includes linear alkanes and cyclic alkanes. Examples of linear alkanes include, but are not limited to, linear alkanes with 2 or more carbons (e.g., ethane, propane, butane, pentane, hexane, heptane, and octane). For example, ethane may be oxidized to form an oxidation product, such as, acetaldehyde, ethanol, methanol, or formaldehyde. Examples of cyclic alkanes include, but are not limited to, cyclic alkanes with 6 or more carbons (e.g., cyclohexane, cycloheptane, cyclooctane). For example, cyclohexane may be oxidized to form an oxidation product such as, cyclohexanol, cyclohexanone, or cyclohexylhydroperoxide.

EXAMPLES

Materials, all available from Sigma—Aldrich®, unless otherwise noted, include manganese (II) chloride tetrahydrate; methanol; sodium peroxide; potassium hexafluorophosphate; sulfuric acid; ethanol; sodium hydroxide; 1,4,7-trimethyl-1,4,7-triazacyclononane (TCI America);

potassium hydroxide; silicon dioxide; acetonitrile; o-dichlorobenzene; cyclohexane; hydrogen peroxide; ethane; terephthalic acid; 3,4-dihydroxyhydrocinnamic acid; titanium dioxide; cerium dioxide; silane:propyltriethoxysilane (Gelest); n-octyltrimethoxysilane (Gelest); mixtures of perfluorododecyl-1H,1H,2H,2H-triethoxysilane and perfluoro-tetradecyl-1H,1H,2H,2H-triethoxysilane (Gelest); mixtures of 1,1,1,3,3,3-hexamethyldisilazane and trimethylchlorosilane and pyridine; 2-(carboxymethoxy)ethyltrimethoxysilane (Gelest); ethyl 4-(triethoxysilyl)benzoate (Gelest).

Support Modified with the Carboxylate Group Synthesis $SiO_2$—C, $SiO_2$—B—Add $SiO_2$ (1-2 grams (g)) and pyridine (50 ml) to a container and stir the contents of the container under nitrogen ($N_2$). Add 2-(carboxymethoxy)ethyltrimethoxysilane or ethyl 4-(triethoxysilyl)benzoate to the contents of the container (1.0 mmol per gram $SiO_2$)), then heat the contents of the container at reflux for 24 hours. Filter solids from the contents of the container, wash solids with pyridine and ether, dry solids under vacuum, and extract solids by soxhlet extraction with benzene for 24 hours. Filter solids, wash solids with ether, and dry solids. Heat the solids for 12-24 hours in refluxing aqueous HCl (25 mL, 1.0 M), then extract solids by soxhlet extraction with water (18 MΩ) to form $SiO_2$—C or $SiO_2$—B with carboxylate group density of 0.07 to 0.80±0.06 groups/nm². Carboxylate group density can be varied by varying the amount of silane ester present during synthesis.

$SiO_2$—C-propyl, $SiO_2$—C-octyl, $SiO_2$—C-perfluoro, $SiO_2$—C-trimethyl—Add $SiO_2$—C and a silane (2.0 mmol silane per g $SiO_2$—C), either propyltriethoxysilane (propyl), n-octyltrimethoxysilane (octyl), commercial mixtures of perfluorododecyl-1H,1H,2H,2H-triethoxysilane/perfluoro-tetradecyl-1H,1H,2H,2H-triethoxysilane (perfluro), or a commercial mixture of 1,1,1,3,3,3-hexamethyldisilazane and trimethylchlorosilane and pyridine (trimethyl), in anhydrous pyridine, to a container. Heat the contents of the container at reflux under $N_2$ for 24 hours to form $SiO_2$—C-propyl, $SiO_2$—C-octyl, $SiO_2$—C-perfluoro, or $SiO_2$—C-trimethyl. Filter solids, extract solids by soxhlet extraction with benzene for 24 hours, and collect the respective supports modified with the carboxylate groups.

$TiO_2$-TA, $CeO_2$-TA, $SiO_2$-TA—Add terephthalic acid (TA) (20 milligrams (mg)), to a borosilicate vial, then cover the TA with a layer of glass wool, followed by a layer of the oxide support, $TiO_2$, $CeO_2$, or $SiO_2$, respectively, and a layer of glass wool. Heat the contents of each borosilicate vial for 5 minutes from 23° C. to 420° C. at a rate of 80° C./min, then cool to 23° C. to form $TiO_2$-TA, $CeO_2$-TA, or $SiO_2$-TA.

Manganese Complex Synthesis

Monomeric manganese complex—Add manganese (II) chloride tetrahydrate (628.2 mg, 3.2 mmol) and methanol (16.8 mL) to a container. Add methanol (67.5 mL) and 1,4,7-trimethyl-1,4,7-triazacyclononane (842.9 mg, 4.0 mmol) to a second container, then mix the contents of the two containers while maintaining at 0° C. Add sodium peroxide (390.9 mg, 5 mmol) to the contents of the container and stir for 1 hour at 0° C., then stir the contents of the container for 45 minutes at 23° C. and add potassium hexafluorophosphate (948.1 mg, 5.2 mmol). Rest the contents of the container for 10 minutes and filter over glass frit. Neutralize filtrate with sulfuric acid (2.0 M) to a pH of 7.24 to quench the reaction. Add water (42 mL) to filtrate and stir for 37 minutes. Filter over glass frit and rinse solids with water. Reduce filtrate volume until solids begin to nucleate. Rinse with water and maintain at 10° C. for 12 hrs to form crystals. Filter crystals with a glass fiber filter and rinse crystals with cold water to form $[(C_6H_{12}N_3R_3)Mn(OX)_3]Z$.

Dimeric manganese complex—Add 1,4,7-trimethyl-1,4,7-triazacyclononane (0.68 g, 4.0 mmol) and 2:1 EtOH/$H_2O$ (8 mL) to a container. Add $MnCl_2$-$4H_2O$ (0.8 g, 1 equivalent (eq)) and $KPF_6$ (1.1 g, 1.5 eq) to the contents of the container and stir for 20 minutes at 50° C. Cool the contents of the container to 0° C. while stirring for 10-15 minutes. Add 1:1 $H_2O_2$ (1.5 M)/NaOH (1.0 M) solution (8.0 mL) to the contents of container and crystallize. Filter and wash crystals with ethanol and ether and dry crystals under vacuum to form $[(C_6H_{12}N_3R_3)Mn_2O_3]Z_2$.

Example (Ex) 1

Synthesize alkane oxidation catalyst in situ and oxidize alkane (cyclohexane) as follows. Add $SiO_2$—C (3.3 mg, 0.6 groups/nm²) in acetonitrile (2 mL) and ($[(C_6H_{12}N_3R_3)Mn_2O_3]Z_2$) (0.2 mM) to a container. The carboxylate group to Mn atom ratio is 0.50:1.0. Add o-dichlorobenzene (100 microliter (μL), 390 mmol) and cyclohexane (50 μL, 200 mmol) to the contents of container and maintain at 0° C. Add $H_2O_2$ (30 weight percent (wt %), 130 μL) to the contents of container. Seal the container and react to produce an alkane oxidation product (cyclohexanone (CyO), cyclohexanol (CyOH), and/or cyclohexyl hydroperoxide (Cy-OOH)). The concentrations of these species are determined as a function of time using gas chromatography and are shown in Table 1.

The turnover number (TON) is the maximum number of substrate (e.g., alkane) molecules that can be converted into product molecules after a given amount of time by a catalyst and is given by the equation:

$$TON \text{ for alkane oxidation catalyst} = \frac{\text{moles alkane oxidation product}}{\text{(moles dimeric manganese complex) or (moles monomeric manganese complex)}}$$

TABLE 1

TON for $[(C_6H_{12}N_3R_3)Mn_2O_3]Z_2$
(0.5 Carboxylate group: 1.0 Mn atom)
Alkane Oxidation Product

| Reaction Time (hr) at 0° C. | CyO | CyOH | Cy-OOH | Total TON (CyO + CyOH + Cy-OOH) |
|---|---|---|---|---|
| 0.3 | 1 | 5 | 1 | 6 |
| 0.5 | 1 | 7 | 1 | 9 |
| 0.8 | 3 | 15 | 1 | 19 |
| 1.5 | 7 | 30 | 2 | 38 |
| 2.0 | 10 | 35 | 0 | 45 |
| 3.0 | 8 | 38 | 1 | 47 |
| 6.0 | 8 | 43 | 2 | 53 |
| 9.0 | 11 | 41 | 0 | 52 |
| 24.3 | 11 | 42 | 0 | 53 |

Exs 2-3

Repeat Ex 1, but with changes: add support modified with the carboxylate group to obtain a carboxylate group to Mn atom ratio of 1.0:1.0 and 3.3:1.0, respectively, to produce an alkane oxidation product, as shown in Tables 2 and 3.

TABLE 2

TON for $[(C_6H_{12}N_3R_3)Mn_2O_3]Z_2$
(1.0 Carboxylate group: 1.0 Mn atom)
Alkane Oxidation Product

| Reaction Time (hr) at 0° C. | CyO | CyOH | Cy-OOH | Total TON (CyO + CyOH + Cy-OOH) |
|---|---|---|---|---|
| 0.3 | 0 | 4 | 1 | 5 |
| 0.5 | 15 | 33 | 0 | 47 |
| 0.8 | 16 | 44 | 12 | 72 |
| 1.0 | 14 | 52 | 16 | 82 |
| 1.5 | 19 | 73 | 14 | 107 |
| 2.0 | 18 | 80 | 28 | 125 |
| 3.0 | 33 | 94 | 5 | 133 |
| 6.0 | 39 | 97 | 5 | 140 |
| 9.0 | 37 | 93 | 5 | 136 |
| 24.2 | 39 | 94 | 6 | 139 |

TABLE 3

TON for $[(C_6H_{12}N_3R_3)Mn_2O_3]Z_2$
(3.3 Carboxylate group: 1.0 Mn atom)
Alkane Oxidation Product

| Reaction Time (hr) at 0° C. | CyO | CyOH | Cy-OOH | Total TON (CyO + CyOH + Cy-OOH) |
|---|---|---|---|---|
| 0.3 | 36 | 31 | 0 | 67 |
| 0.5 | 51 | 57 | 0 | 108 |
| 0.8 | 48 | 70 | 26 | 145 |
| 1.0 | 37 | 89 | 67 | 193 |
| 1.5 | 48 | 145 | 82 | 274 |
| 2.0 | 46 | 163 | 88 | 296 |
| 3.0 | 62 | 168 | 78 | 308 |
| 6.3 | 102 | 183 | 40 | 326 |
| 9.0 | 116 | 172 | 28 | 315 |
| 23.3 | 107 | 256 | 57 | 420 |

Calculate TON for $[(C_6H_{12}N_3R_3)Mn_2O_3]Z_2$ with data from Exs 1-3. The data in Tables 1-3 show that the alkane oxidation catalyst forms in situ and that an oxidation product forms. The data in Tables 1-3 show that formation of the oxidation product increases with the carboxylate group to Mn atom ratio.

Ex 4

Repeat Ex 1, but with changes: add monomeric manganese complex (0.2 mM), rather than dimeric manganese complex; use $SiO_2$—C (0.03±0.06 groups/$nm^2$); and adjust the carboxylate group to Mn atom ratio to 0.3:1.0. React for 3 hours.

Exs 5-7

Repeat Ex 4, but with changes: adjust the carboxylate group to Mn atom ratio to 0.5:1.0, 1.0:1.0, and 1.9:1.0, respectively.

Ex 8

Repeat Ex 4, but with changes: use $SiO_2$—C (0.2 groups/$nm^2$); and adjust the carboxylate group to Mn atom ratio to 3.3:1.0.

Exs 9-11

Repeat Ex 4, but with changes: use $SiO_2$—C (0.25 groups/$nm^2$); and adjust the carboxylate group to Mn atom ratio to 1.1:1.0, 2.0:1.0, and 4.1:1.0, respectively.

Ex 12

Repeat Ex 4, but with changes: use $SiO_2$—C (0.41 groups/$nm^2$); and adjust the carboxylate group to Mn atom ratio to 6.8:1.0.

Ex 13-15

Repeat Ex 4, but with changes: use $SiO_2$—C (0.59 groups/$nm^2$); and adjust the carboxylate group to Mn atom ratio to 1.0:1.0, 10:1.0, and 10:1.0, respectively.

TABLE 4

| Example number | Carboxylate groups/$nm^2$ | Carboxylate group/Mn Atom | Total TON (CyO + CyOH + Cy-OOH) for $[(C_6H_{12}N_3R_3)Mn(OX)_3]Z$ |
|---|---|---|---|
| Ex 4 | 0.03 | 0.3:1.0 | 69 |
| Ex 5 | 0.03 | 0.5:1.0 | 128 |
| Ex 6 | 0.03 | 1.0:1.0 | 91 |
| Ex 7 | 0.03 | 1.9:1.0 | 198 |
| Ex 8 | 0.20 | 3.3:1.0 | 185 |
| Ex 9 | 0.25 | 1.1:1.0 | 72 |
| Ex 10 | 0.25 | 2.0:1.0 | 157 |
| Ex 11 | 0.25 | 4.1:1.0 | 269 |
| Ex 12 | 0.41 | 6.8:1.0 | 273 |
| Ex 13 | 0.59 | 1.0:1.0 | 41 |
| Ex 14 | 0.59 | 10:1.0 | 58 |
| Ex 15 | 0.59 | 10:1.0 | 172 |

Calculate Total TON for $[(C_6H_{12}N_3R_3)Mn(OX)_3]Z$ with data from Exs 4-15. Calculate total TON as:

$$\text{Total TON} = \text{TON(CyO)} + \text{TON(CyOH)} + \text{TON(Cy-OOH)}$$

The data in Table 4 show that the alkane oxidation catalyst forms in situ and that an alkane oxidation product forms. The data in Table 4 show that lower carboxylate surface density increases formation of alkane oxidation products for a given total carboxylate content and that formation of alkane oxidation products increases with increasing total carboxylate content.

Exs 16-18

Repeat Ex 1, but with changes: use $SiO_2$—C (0.03 groups/$nm^2$); and adjust the carboxylate group to Mn atom ratio to 0.5:1.0, 1.0:1.0, 1.9:1.0, respectively.

Ex 19

Repeat Ex 1, but with changes: use $SiO_2$—C (0.2 groups/$nm^2$); and adjust the carboxylate group to Mn atom ratio to 3.2:1.0.

Exs 20-22

Repeat Ex 1, but with changes: use $SiO_2$—C (0.25 groups/$nm^2$); and adjust the carboxylate group to Mn atom ratio to 1.0:1.0, 1.9:1.0, 4.0:1.0, respectively.

Ex 23

Repeat Ex 1, but with changes: use $SiO_2$—C (0.41 groups/$nm^2$); and adjust the carboxylate group to Mn atom ratio to 6.5:1.0.

Exs 24-25

Repeat Ex 1, but with changes: use $SiO_2$—C (0.59 groups/$nm^2$); and adjust the carboxylate group to Mn atom ratio to 1.0:1.0 and 10:1.0, respectively.

TABLE 5

| Example number | Carboxylate groups/nm$^2$ | Carboxylate group/Mn Atom | Total TON (CyO + CyOH + Cy-OOH) for [(C$_6$H$_{12}$N$_3$R$_3$)Mn$_2$O$_3$]Z$_2$ |
|---|---|---|---|
| Ex 16 | 0.03 | 0.50:1.0 | 136 |
| Ex 17 | 0.03 | 1.0:1.0 | 128 |
| Ex 18 | 0.03 | 1.9:1.0 | 189 |
| Ex 19 | 0.20 | 3.2:1.0 | 184 |
| Ex 20 | 0.25 | 1.0:1.0 | 103 |
| Ex 21 | 0.25 | 1.9:1.0 | 161 |
| Ex 22 | 0.25 | 4.0:1.0 | 194 |
| Ex 23 | 0.41 | 6.5:1.0 | 236 |
| Ex 24 | 0.59 | 1.0:1.0 | 39 |
| Ex 25 | 0.59 | 10:1.0 | 171 |

Calculate Total TON for [(C$_6$H$_{12}$N$_3$R$_3$)Mn$_2$O$_3$]Z$_2$ with data from Exs 16-25. The data in Table 5 show that the alkane oxidation catalyst forms in situ and that an oxidation product forms. The data in Table 5 show that lower carboxylate surface density increases formation of oxidation products for a given total carboxylate content and that formation of alkane oxidation products increases with increasing total carboxylate content.

Ex 26

Obtain alkane oxidation catalyst in situ and oxidize alkane as follows. Add SiO$_2$—C (1.3 mg, 0.6 groups/nm$^2$) in acetonitrile (50 mL) and dimeric manganese complex (4.17 mg, 1.0 mM) to a container. The carboxylate group to Mn atom ratio is 6.5:1.0. Seal the container and bring the contents of the container to 0° C. Add H$_2$O$_2$ (30 wt %, 2.7 mL), resulting in a total H$_2$O$_2$ concentration of 0.5 M. Pressurize container to 50 pounds per square inch (psi) with ethane and maintain ethane source to produce an alkane oxidation product (ethanol (EtOH), methanol (MeOH), and/or acetaldehyde (MeCHO)), as shown in Table 6. Take samples from a dip tube with glass fit placed in the container. Condense alkane oxidation products into GC vials held at −196.15° C.

TABLE 6

| Reaction Time (hr) at 0° C. | TON for [(C$_6$H$_{12}$N$_3$R$_3$)Mn$_2$O$_3$]Z$_2$ (6.5 Carboxylate group: 1.0 Mn atom) Alkane Oxidation Product | | | |
|---|---|---|---|---|
| | EtOH | MeOH | MeCHO | Total TON |
| 0.5 | 1.3 | 0.0 | 0.0 | 1 |
| 0.8 | 2.0 | 0.0 | 0.5 | 3 |
| 1.0 | 2.5 | 0.0 | 0.6 | 3 |
| 3.0 | 11.6 | 1.0 | 2.9 | 16 |
| 5.0 | 16.4 | 1.3 | 4.7 | 23 |
| 7.0 | 18.9 | 1.6 | 5.8 | 26 |
| 9.0 | 23.6 | 2.1 | 7.8 | 34 |
| 11.0 | 25.2 | 2.6 | 9.0 | 37 |
| 13.0 | 29.6 | 2.8 | 11.8 | 44 |
| 15.0 | 30.8 | 3.1 | 12.8 | 47 |
| 17.0 | 30.7 | 3.0 | 15.8 | 50 |
| 23.0 | 35.4 | 4.3 | 19.1 | 59 |
| 25.0 | 36.7 | 4.0 | 19.3 | 60 |

Calculate TON for [(C$_6$H$_{12}$N$_3$R$_3$)Mn$_2$O$_3$]Z$_2$ with data from Ex 26. The data in Table 6 show that the alkane oxidation catalyst forms in situ and that an oxidation product forms.

Ex 27

Repeat Ex 26, but with changes: equilibrate the reaction vessel to 24° C., rather than 0° C., to produce an oxidation product, as shown in Table 7.

TABLE 7

| Reaction Time (hr) at 24° C. | TON for [(C$_6$H$_{12}$N$_3$R$_3$)Mn$_2$O$_3$]Z$_2$ (6.5 Carboxylate group: 1.0 Mn atom) Alkane Oxidation Product | | | |
|---|---|---|---|---|
| | EtOH | MeOH | MeCHO | Total TON |
| 0.3 | 3.8 | 0.0 | 0.9 | 5 |
| 0.6 | 5.3 | 0.0 | 1.6 | 7 |
| 0.8 | 8.4 | 0.0 | 2.2 | 11 |
| 1.0 | 9.6 | 0.0 | 2.7 | 12 |
| 1.6 | 11.7 | 0.0 | 3.5 | 15 |
| 2.0 | 15.6 | 0.0 | 4.5 | 20 |
| 2.9 | 23.3 | 1.3 | 6.2 | 31 |
| 5.0 | 27.4 | 1.3 | 7.8 | 36 |
| 6.9 | 30.5 | 1.7 | 8.6 | 41 |
| 8.9 | 30.8 | 1.8 | 9.3 | 42 |
| 11.5 | 31.9 | 2.1 | 9.8 | 44 |
| 13.3 | 31.5 | 1.9 | 9.5 | 43 |
| 15.0 | 33.3 | 2.3 | 10.1 | 46 |
| 17.0 | 30.9 | 2.0 | 9.7 | 43 |
| 21.0 | 31.7 | 2.0 | 9.8 | 44 |
| 23.1 | 31.1 | 2.2 | 9.6 | 43 |
| 24.6 | 30.3 | 1.9 | 9.8 | 42 |

Calculate TON for [(C$_6$H$_{12}$N$_3$R$_3$)Mn$_2$O$_3$]Z$_2$ using data from Ex 27. The data in Table 7 show that the alkane oxidation catalyst forms in situ and that an oxidation product forms. Data in Table 7 from Ex 26, performed at 0° C., in comparison with data in Table 7 from Ex 27, performed at 24° C., show that reaction rates increase at 24° C.

Ex 28

Repeat Ex 27, but with changes: add monomeric manganese complex (2.45 mg, 1.0 mM), rather than dimeric manganese complex (4.17 mg, 1.0 mM) and add SiO2-C (0.65 g, 0.6 groups/nm$^2$) to produce an oxidation product, as shown in Table 8.

TABLE 8

| Reaction Time (hr) at 24° C. | TON for [(C$_6$H$_{12}$N$_3$R$_3$)Mn(OX)$_3$]Z (6.5 Carboxylate group: 1.0 Mn atom) Alkane Oxidation Product | | | |
|---|---|---|---|---|
| | EtOH | MeOH | MeCHO | Total TON |
| 0.3 | 2.2 | 0.0 | 0.0 | 2 |
| 0.5 | 3.5 | 0.0 | 0.5 | 4 |
| 0.7 | 4.7 | 0.0 | 0.8 | 5 |
| 1.0 | 5.9 | 0.0 | 1.1 | 7 |
| 1.6 | 7.5 | 0.0 | 1.4 | 9 |
| 2.0 | 8.9 | 0.0 | 1.6 | 11 |
| 3.0 | 10.9 | 0.0 | 2.1 | 13 |
| 5.0 | 12.1 | 0.0 | 2.0 | 14 |
| 7.1 | 13.4 | 0.0 | 2.2 | 16 |
| 24.2 | 12.9 | 0.0 | 2.2 | 15 |

Calculate TON for [(C$_6$H$_{12}$N$_3$R$_3$)Mn(OX)$_3$]Z with data from Ex 28. The data in Table 8 show that the alkane oxidation catalyst forms in situ and that an oxidation product forms.

Ex 29

Repeat Ex 1, but with changes: use SiO$_2$—C (0.25 groups/nm$^2$) and adjust the dimeric manganese complex concentration to 0.282 mM.

Ex 30

Repeat Ex 1, but with changes: use SiO$_2$—C-trimethyl, rather than SiO$_2$—C (0.59 groups/nm$^2$) and adjust the dimeric manganese complex concentration to 0.129 mM.

Ex 31

Repeat Ex 30, but with changes: use $SiO_2$—C-octyl, rather than $SiO_2$—C-trimethyl (0.40 groups/nm$^2$).

Ex 32

Repeat Ex 30, but with changes: use $SiO_2$—C-perfluro, rather than $SiO_2$—C-trimethyl (0.40 groups/nm$^2$).

Ex 33

Repeat Ex 30, but with changes: add $TiO_2$-TA, rather than $SiO_2$—C-trimethyl (0.22 groups/nm$^2$).

Ex 34

Repeat Ex 30, but with changes: add $CeO_2$-TA, rather than $SiO_2$—C-trimethyl (0.13 groups/nm$^2$).

Ex 35

Repeat Ex 30, but with changes: add $SiO_2$-TA, rather than $SiO_2$—C-trimethyl (0.60 groups/nm$^2$).

Ex 36

Repeat Ex 30, but with changes: add $SiO_2$—B, rather than $SiO_2$—C-trimethyl (0.32 groups/nm$^2$).

Ex 38

Repeat Ex 4, but with changes: use $SiO_2$—C-trimethyl, rather than $SiO_2$—C (0.59 groups/nm$^2$) and adjust the monomeric manganese complex concentration to 0.128 mM.

Ex 39

Repeat Ex 38, but with changes: use $SiO_2$—C-octyl, rather than $SiO_2$—C-trimethyl (0.40 groups/nm$^2$).

Ex 40

Repeat Ex 38, but with changes: use $SiO_2$—C-perfluro, rather than $SiO_2$—C-trimethyl (0.40 groups/nm$^2$).

Ex 41

Repeat Ex 38, but with changes: use $TiO_2$-TA, rather than $SiO_2$—C-trimethyl (0.22 groups/nm$^2$).

Ex 42

Repeat Ex 38, but with changes: use $CeO_2$-TA, rather than $SiO_2$—C-trimethyl (0.13 groups/nm$^2$).

TABLE 9

| Example number | Support modified with the carboxylate group | Support | Carboxylate groups/support area (groups/nm$^2$) | Alkane oxidation catalyst concentration mM | TON for Dimeric Mn complex to CyOH, CyO, and CyOOH (0° C.) CyOH | CyO | CyOOH | Total TON | CyOH/CyO Selectivity |
|---|---|---|---|---|---|---|---|---|---|
| Ex 29 | SiO2—C | SiO2 | 0.25 | 0.282 | 91 | 42 | 27 | 160 | 2.2 |
| Ex 30 | SiO2—C-trimethyl | SiO2—(CH3)3 | 0.59 | 0.129 | 20 | 5 | 2 | 27 | 3.7 |
| Ex 31 | SiO2—C-octyl | SiO2—C8 | 0.40 | 0.129 | 92 | 28 | 53 | 172 | 3.3 |
| Ex 32 | SiO2—C-perfluoro | SiO2—F | 0.40 | 0.129 | 38 | 8 | 0 | 45 | 4.8 |
| Ex 33 | TiO2-TA | TiO2 | 0.22 | 0.129 | 83 | 38 | 65 | 186 | 2.2 |
| Ex 34 | CeO2-TA | CeO2 | 0.13 | 0.129 | 42 | 35 | 77 | 154 | 1.2 |
| Ex 35 | SiO2-TA | SiO2 | 0.60 | 0.129 | 56 | 36 | 90 | 183 | 1.5 |
| Ex 36 | SiO2—B | SiO2 | 0.32 | 0.129 | 45 | 9 | 0 | 54 | 5.0 |

Calculate CyOH/CyO selectivities with data from Exs 29-36. The data in Table 9 show that the alkane oxidation catalyst forms in situ when using co-catalysts different than $SiO_2$—C and that an oxidation product forms. The data in Table 9 show that several co-catalysts deactivate the dimeric complex relative to when $SiO_2$—C is used; these also raise alcohol selectivities.

Ex 37

Repeat Ex 4, but with changes: use $SiO_2$—C (0.59 groups/nm$^2$) and adjust the monomeric manganese complex concentration to 0.108 mM.

Ex 43

Repeat Ex 38, but with changes: use $SiO_2$-TA, rather than $SiO_2$—C-trimethyl (0.60 groups/nm$^2$).

Ex 44

Repeat Ex 38, but with changes: use $SiO_2$—B, rather than $SiO_2$—C-trimethyl (0.32 groups/nm$^2$).

TABLE 10

| Example number | Support modified with the carboxylate group | Support | Carboxylate groups/support area (groups/nm$^2$) | Alkane oxidation catalyst concentration mM | TON for Monomeric Mn complex to CyOH, CyO, and CyOOH (0° C.) | | | Total TON | CyOH/CyO Selectivity |
|---|---|---|---|---|---|---|---|---|---|
| | | | | | CyOH | CyO | CyOOH | | |
| Ex 37 | SiO2—C | SiO2 | 0.590 | 0.108 | 15 | 4 | 3 | 22 | 3.5 |
| Ex 38 | SiO2—C-trimethyl | SiO2—(CH3)3 | 0.590 | 0.128 | 18 | 3 | 0 | 21 | 5.2 |
| Ex 39 | SiO2—C-octyl | SiO2—C8 | 0.400 | 0.128 | 38 | 6 | 0 | 44 | 6.1 |
| Ex 40 | SiO2—C-perfluoro | SiO2—F | 0.400 | 0.128 | 22 | 4 | 0 | 26 | 5.8 |
| Ex 41 | TiO2-TA | TiO2 | 0.220 | 0.128 | 41 | 7 | 0 | 49 | 5.6 |
| Ex 42 | CeO2-TA | CeO2 | 0.130 | 0.128 | 26 | 5 | 0 | 32 | 4.9 |
| Ex 43 | SiO2-TA | SiO2 | 0.600 | 0.128 | 53 | 6 | 5 | 63 | 8.5 |
| Ex 44 | SiO2—B | SiO2 | 0.320 | 0.128 | 21 | 4 | 0 | 24 | 5.6 |

Calculate CyOH/CyO selectivities with data from Exs 37-44. The data in Table 10 show that the alkane oxidation catalyst forms in situ when using co-catalysts different than SiO$_2$—C and that an oxidation product forms.

What is claimed is:

1. An alkane oxidation catalyst comprising:
   a support modified with a carboxylate group, where the carboxylate group is functionalized with a manganese complex selected from the group consisting of [(C$_6$H$_{12}$N$_3$R$_3$)Mn(OCH$_3$)$_3$]Z, [(C$_6$H$_{15}$N$_3$)Mn$_4$O$_6$]Z$_4$, or a combination thereof, where each R is independently an alkyl group having 1 to 3 carbons, and each Z is independently PF$_6^-$, ClO$_4^-$, or Br$^-$.

2. The oxidation catalyst of claim 1, where the support is selected from the group consisting of an oxide support, a carbon support, or a combination thereof.

3. The oxidation catalyst of claim 1, where the manganese complex and the carboxylate group have a molar ratio in a range of from 1:0.3 to 1:20.

4. A method for oxidizing an alkane:
   contacting a support modified with a carboxylate group with a manganese complex selected from the group consisting of [(C$_6$H$_{12}$N$_3$R$_3$)Mn(OCH$_3$)$_3$]Z, [(C$_6$H$_{12}$N$_3$R$_3$)Mn$_2$O$_3$]Z$_2$, [(C$_6$H$_{15}$N$_3$)Mn$_4$O$_6$]Z$_4$, or a combination thereof, where each R is independently an alkyl group having 1 to 3 carbons, and each Z is independently PF$_6^-$, ClO$_4^-$, or Br$^-$— and hydrogen peroxide to functionalize the carboxylate group with the manganese complex to form an alkane oxidation catalyst; and
   oxidizing the alkane by contacting the alkane with the alkane oxidation catalyst in the presence of the hydrogen peroxide to provide a product selected from the group consisting of alcohols, ketones, aldehydes, alkylhydroperoxides, or a combination thereof.

5. The method of claim 4, where the alkane is selected from the group consisting of ethane, cyclohexane, or a combination thereof.

6. The method of claim 5, where the alkane is cyclohexane and the product is selected from the group consisting of cyclohexanol, cyclohexanone, cyclohexylhydroperoxide, or a combination thereof.

7. The method of claim 5, where the alkane is ethane and the product is selected from the group consisting of acetaldehyde, ethanol, methanol, formaldehyde, or a combination thereof.

8. The method of claim 4, wherein oxidizing the alkane occurs at a temperature in a range of from −10 degrees Celsius to 50 degrees Celsius.

9. The method of claim 4, where contacting the support modified with the carboxylate group with the manganese complex and the hydrogen peroxide occurs in the presence of a solvent, where the solvent is selected from the group consisting of acetonitrile, water, methanol, acetic acid, acetone, or a combination thereof.

10. The method of claim 4, where the hydrogen peroxide and the alkane have a molar ratio in a range of from 3:1 to 1:20.

* * * * *